United States Patent
Dittmar et al.

(10) Patent No.: US 7,426,872 B2
(45) Date of Patent: Sep. 23, 2008

(54) SENSOR, DEVICE AND METHOD FOR MEASURING THE PRESSURE OF AN INTERFACE BETWEEN TWO BODIES

(75) Inventors: André Dittmar, Lyons (FR); Georges Delhomme, Saint Laurent de Mure (FR); Claudine Gehin, Mions (FR)

(73) Assignees: Centre National de la Recherche Scientifique, Paris (FR); Institut National des Sciences Appliquees de Lyon, Villeurbanne (FR)

( * ) Notice: Subject to any disclaimer, the term of this patent is extended or adjusted under 35 U.S.C. 154(b) by 0 days.

(21) Appl. No.: 10/566,701

(22) PCT Filed: Jul. 29, 2004

(86) PCT No.: PCT/FR2004/002037

§ 371 (c)(1),
(2), (4) Date: Nov. 20, 2006

(87) PCT Pub. No.: WO2005/012863

PCT Pub. Date: Feb. 10, 2005

(65) Prior Publication Data

US 2007/0062301 A1    Mar. 22, 2007

(30) Foreign Application Priority Data

Aug. 1, 2003 (FR) .................................. 03 09570

(51) Int. Cl.
*G01N 3/08* (2006.01)
(52) U.S. Cl. ...................................................... 73/818
(58) Field of Classification Search .................... 73/818
See application file for complete search history.

(56) References Cited

U.S. PATENT DOCUMENTS

| | | | |
|---|---|---|---|
| 3,785,381 A | | 1/1974 | Lower et al. |
| 3,824,709 A | | 7/1974 | Knapp et al. |
| 4,593,703 A | | 6/1986 | Cosman |
| 4,651,433 A | * | 3/1987 | Mohr .......................... 33/367 |
| 4,823,619 A | | 4/1989 | D'Antonio et al. |
| 4,982,611 A | | 1/1991 | Lorenz et al. |
| 5,688,118 A | | 11/1997 | Hayka et al. |
| 5,983,727 A | * | 11/1999 | Wellman et al. .............. 73/724 |

(Continued)

FOREIGN PATENT DOCUMENTS

DE        102 02 503 A1        7/2003

(Continued)

OTHER PUBLICATIONS

Silveira et al., "Instrumentedan Obstetrical Forceps," IEEE ICIT'02, Bangkok, Thailand, 2002, pp. 470-473.

*Primary Examiner*—Max Noori
(74) *Attorney, Agent, or Firm*—MH2 Technology Law Group LLP

(57) ABSTRACT

The present invention relates to a sensor (10) for sensing the interface pressure between two bodies, the sensor having at least two intercommunicating detection zones (11), each detection zone being formed inside an inflatable envelope (12) for interposing between said bodies and having two opposite regions whose spacing apart depends on the interface pressure between said bodies, each detection zone including a detector (15*a*, 15*b*) arranged to deliver information associated with the spacing between the opposite regions (12*a*, 12*b*).

32 Claims, 8 Drawing Sheets

U.S. PATENT DOCUMENTS

| | | | |
|---|---|---|---|
| 6,019,728 A * | 2/2000 | Iwata et al. | 600/486 |
| 6,058,781 A * | 5/2000 | Kasuyama et al. | 73/724 |
| 6,102,617 A * | 8/2000 | Hampton | 405/52 |
| 6,367,106 B1 | 4/2002 | Gronsman | |
| 6,393,919 B1 * | 5/2002 | Ohji et al. | 73/708 |
| 6,625,029 B2 * | 9/2003 | Bernini | 361/728 |
| 6,688,180 B1 * | 2/2004 | Lund et al. | 73/708 |
| 6,773,095 B2 * | 8/2004 | Isono | 347/72 |
| 6,855,158 B2 * | 2/2005 | Stolpmann | 607/108 |
| 6,892,583 B2 * | 5/2005 | Baek | 73/715 |
| 2005/0014115 A1 | 1/2005 | Riener et al. | |

FOREIGN PATENT DOCUMENTS

| | | |
|---|---|---|
| GB | 2 122 746 A | 1/1984 |
| GB | 2 199 953 A | 7/1988 |
| WO | WO 03/001482 A3 | 1/2003 |
| WO | WO 03/041034 | 5/2003 |
| WO | WO 2005/013239 A2 | 2/2005 |

* cited by examiner

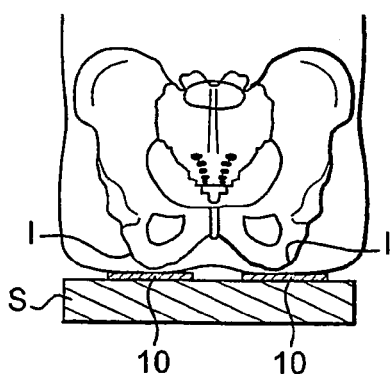
Fig. 25
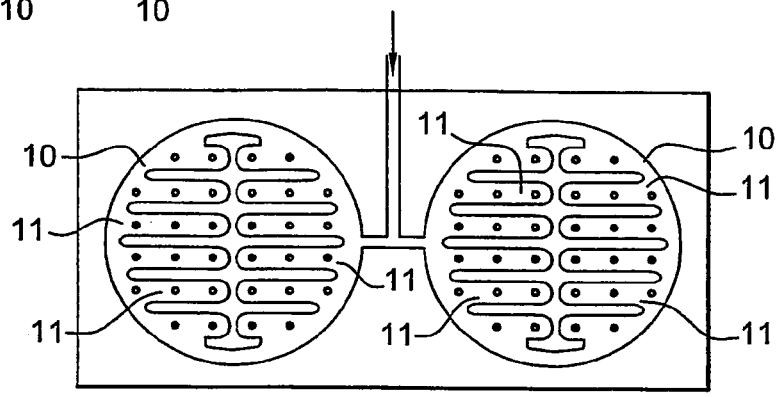
Fig. 26
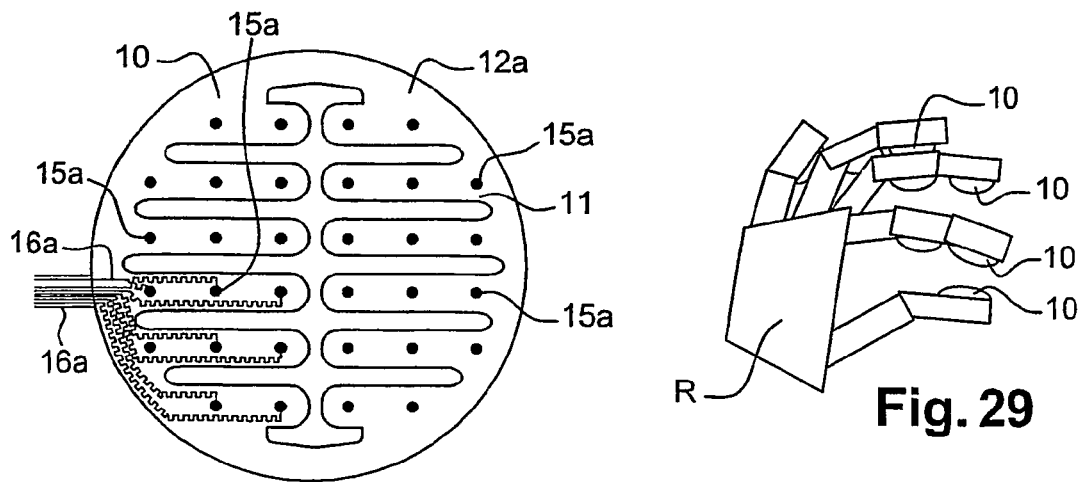
Fig. 27
Fig. 29
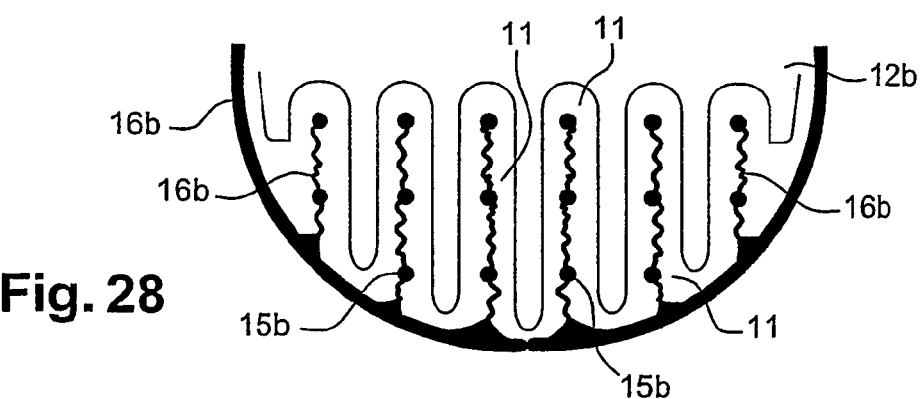
Fig. 28

SENSOR, DEVICE AND METHOD FOR MEASURING THE PRESSURE OF AN INTERFACE BETWEEN TWO BODIES

The present invention relates to methods and apparatuses for measuring the interface pressure between two bodies.

BACKGROUND OF THE INVENTION

British patent application GB 2 199 953 describes a pressure measuring device including a cell constituted by an inflatable envelope having two opposite regions whose outside faces are for coming into contact with respective surfaces between which it is desired to measure the interface pressure. Electrical conductors disposed on the inside faces of said regions can come into contact when the pressure exerted on the envelope exceeds the pressure that exists within the envelope.

OBJECT AND SUMMARY OF THE INVENTION

There exists a need to benefit from improved means enabling an interface pressure to be measured, more compactly, in reliable manner, and at relatively low cost.

The invention seeks in particular to satisfy this need.

In one of its aspects, the invention provides a sensor for sensing the interface pressure between two bodies, which sensor may include at least two intercommunicating detection zones, each detection zone being formed inside an inflatable envelope for interposing between said bodies, and having two opposite regions whose spacing apart depends on the interface pressure between said bodies, each detection zone including a detector arranged to deliver information associated with the spacing between said regions.

The term "intercommunicating detection zones" is used to designate detection zones that are interconnected in such a manner as to enable the pressure of a fluid filling said detection zones to come into equilibrium, it being possible for the fluid to flow, where necessary, from one detection zone to the other.

By means of the invention, it is possible to inflate the set of detection zones from a single fluid source, thus making it possible to achieve savings in space, greater reliability, and lower cost, in particular to such an extent as to be compatible with certain applications in which the sensor needs to be for single use only.

In addition, the invention makes it possible to make sensors having a large number of detection zones, thus making it possible to use such sensors in a very wide variety of applications.

The number of detection zones of a sensor may lie in particular in the range 2 to 100, or even several hundreds depending on the application.

At least one envelope of a detection zone can be made at least in part out of an elastically deformable material. The use of such a material can make it easier to ensure that the envelope does not significantly modify the interface pressure existing between the two bodies, and in particular does not lead to excessive levels of stress or shear forces.

The envelope of at least one detection zone may advantageously be made of a membrane, in particular an elastomer membrane, of small thickness, in particular having a thickness that is less than or equal to 1 millimeter (mm) and in particular less than or equal to 0.5 mm, or even about 0.1 mm, which presents the particular advantage of making it adaptable to a large number of bodies presenting a variety of shapes.

At least one detection zone may present a shape that is selected in such a manner that the presence of the sensor between the two bodies does not significantly modify the interface pressure that exists between them. By way of example, when seen from above, a detection zone may have a shape that is circular, square, or rectangular, or some other shape.

By way of example, each of the opposite regions of the envelope may have an area that is less than or equal to 100 square centimeters ($cm^2$) or even less than or equal to 10 $cm^2$, and in particular may lie in the range 0.1 $cm^2$ to 1 $cm^2$.

One of the facing regions of the envelope may extend over an area that is greater than that of the surface of the body with which it comes into contact.

The detection zones may be arranged in various ways, for example linearly or in a two-dimensional array, or even a three-dimensional array, e.g. as a function of the shape of the surface of the body against which they come to bear.

A detection zone may include at least one wall in common with at least one adjacent detection zone, said common wall possibly including at least one passage enabling the detection zones to communicate with each other.

In a variant, or in addition, communication between two adjacent detection zones may be established via at least one duct that is external to the detection zones.

In another variant, no partition separates two adjacent detection zones.

At least one detection zone may include a detector arranged to measure the spacing between the two facing regions of the envelope in said detection zone, e.g. by delivering a signal that is proportional to said spacing.

At least one detector of at least one detection zone may be selected from the following list: an electrical detector, in particular a contact or a capacitance electrical detector; an optical detector, in particular an optical fiber detector, a diffraction detector, or an optical focus detector; a magnetic detector, in particular an induction detector, a linear wire or coil detector, or a Hall effect detector; or a thermal detector.

A detector may include at least two elements disposed respectively on each of the inside faces of facing regions of the envelope of the detection zone.

By way of example, an electrical contact detector may comprise at least two electrical conductors disposed respectively on each of the two inside faces of said facing regions of the envelope of the detection zone. The information delivered by such a detector corresponds to making an electrical contact between the conductors, or to breaking said contact.

By way of example, a capacitive detector comprises two electrodes disposed on respective ones of the inside faces of facing regions of the envelope. The information delivered by such a detector corresponds to the capacitance of the capacitor formed by the electrodes, which capacitance depends on the spacing between said regions. Such a detector can serve to measure the spacing between the regions.

An optical fiber detector may comprise at least two optical fibers e.g. disposed on the respective inside faces of two facing regions of the envelope of the detection zone. When the fibers are aligned along a common axis, i.e. when the two regions are in contact, a light beam is passed from one to the other, whereas when the fibers are not in alignment, i.e. when the regions are spaced apart, a light beam no longer passes.

An optical focusing detector comprises two optical fibers and a lens enabling the light beam to be concentrated, thus making it possible to obtain information that is relatively precise.

A diffraction detector comprises a light emitter and a light receiver, together with a diffraction element situated in the space between the facing regions. The light intensity received by the receiver is a function of the spacing between the regions.

An induction detector comprises a coil or a linear wire for emitting a magnetic field that varies in time, and a coil or a wire for receiving said magnetic field, and disposed respectively on each of the inside faces of facing regions of the envelope of the detection zone. The information delivered by such a detector corresponds to the voltage induced by one of the elements in the other, which depends in particular on the spacing of said regions.

A Hall effect detector comprises a magnetic element and a Hall effect probe respectively disposed on each of the inside faces of the facing regions of the envelope of the detection zone. Such a detector can serve to measure the spacing between said opposite regions.

A thermal detector comprises at least one hot element and a detector element that is temperature-sensitive. The information delivered by the detector can correspond to thermal contact being made or broken between the two elements.

Other detectors can also be used without that going beyond the ambit of the present invention.

In a particular embodiment, the detector associated with a detection zone may include both a portion of an element that is common to a plurality, or even to all, of the detection zones, and an element that is specific to said detection zone. For example, an electrical contact detector associated with a detection zone may comprise a portion of an electrical conductor that is common to a plurality or even all of the detection zones, said conductor being connected to an electrical ground, for example, together with an electrical conductor that is specific to said detection zone.

The information associated with the spacing between the facing regions of the envelope as delivered by the detector of a detection zone may be analog or digital, e.g. binary, and may indicate whether the two facing regions of the envelope of said detection zone are or are not substantially in contact with each other, for example. In a first configuration of the detection zone, the facing regions of the envelope are in contact with each other and the pressure inside the detection zone is less than the interface pressure between the two bodies at the location of said detection zone. In a second configuration, the facing regions of the envelope are not in contact with each other, the pressure inside the detection zone being greater than the interface pressure between the two bodies at said location. At the moment when the detection zone passes from one configuration to the other, the pressure inside the detection zone is substantially equal to the interface pressure between the two bodies at the location of said detection zone.

For an electrical contact detector, the information that is delivered may correspond to contact being broken or made.

The information delivered by a detector is renewed each time the detector changes state. For example, for an electrical contact detector, the information delivered is renewed each time the detector passes from the configuration in which the electrical conductors are making contact, to the configuration in which the electrical contact between the electrical conductors is broken, in which case the electrical conductors are spaced apart from each other.

The detector of a detection zone is preferably configured substantially to preserve the interface pressure between the two bodies and avoid introducing stresses or shear forces that would excessively disturb the results of the analysis.

At least one detection zone may include a detector including an element, in particular a non-linear electrical conductor, in particular an electrical conductor extending in a zigzag. In particular, for a detection element, in particular an electrical conductor, that is common to all of the detection zones, or at least to some of them, the conductor may present a zigzag shape so as to avoid introducing excessive shear forces or stresses, and thus avoid modifying the pressure between the bodies.

The zigzag configuration of an electrical conductor may also serve to increase the sensitivity of the detector when the two facing regions of the envelope move towards each other, by enabling a plurality of contact points to be made between the two conductors disposed respectively in said region. Thus, contact between the electrical conductors may be detected as soon as contact is made with one of these contact points. If the facing regions of the envelope are in partial contact with each other, it is then nevertheless possible to detect contact. The contact zone may be provided with a conductive pellet, e.g. made of Ag, Au, or Be, for the purpose of reducing contact resistance and of increasing contact durability.

By way of example, the electrical conductors may be made by etching a flexible medium coated in a metal conductor.

The sensor may include a fluid admission that is common to all of the detection zones of the sensor. The fluid may be a gas, e.g. air, nitrogen, argon, or any inert biocompatible medical gas, or it may be a liquid, e.g. water, physiological serum, oil, or any inert biocompatible biomedical fluid.

The sensor may also include at least one fluid admission external to the detection zones and serving each of them from the outside, so as to make it possible in particular for all of the detection zones to be more easily sensitive to the same pressure at the same time.

The sensor may be arranged in such a manner as to be capable of being thoroughly sterilized, in particular by being raised to a temperature greater than or equal to 130° C. Under such circumstances, the envelope of each detection zone may advantageously be made of a plastics material that withstands high temperatures.

The detection zones of the sensor may be secured on a support, e.g. an elastomer support or a stretchable textile support, in particular of the knit type.

In another of its aspects, the invention provides apparatus for measuring the interface pressure between two bodies, the apparatus being characterizable by the fact that it includes a sensor as defined above.

Such apparatus may also include a pressure generator arranged to deliver fluid under a pressure that is variable in time into the detection zones of the sensor. The apparatus may be arranged in such a manner that at a given instant all of the detection zones are at substantially the same pressure.

The pressure generator may be arranged in such a manner as to cause the pressure to vary in application of a function that is periodic and continuous, in particular sinusoidal or a sawtooth function. The maximum pressure and the minimum pressure may correspond respectively to the highest pressure and the lowest pressure detected by two of the detection zones in the set of detection zones. In a variant, the maximum pressure and the minimum pressure may be predetermined.

The pressure generator may be arranged so that the pressure varies around a mean value that corresponds substantially to the interface pressure.

In a variant, the pressure-measuring apparatus may be arranged to detect the last separation between facing zones of a detection zone in the set of detection zones, and then to cause the pressure generator to reduce the applied pressure.

This makes it possible to shorten the duration of a cycle. In addition, the pressure applied does not exceed the pressure that is needed for separating the regions, thus serving to avoid stretching the membrane of the sensor pointlessly.

The apparatus may include a system for processing the information delivered by the detector of at least detection zone, and preferably for processing the information delivered by the detectors of the detection zones.

By way of example, the processor system may be arranged to respond to information delivered by the detector of a detection zone to determine the interface pressure between the two bodies at a given instant at the location of said detection zone.

Information delivered by a detector of a detection zone enables the processor system to update the value for the interface pressure at said instant and at the location of said detection zone.

This value is considered as being the value for the interface pressure at the location of said detection zone until new information is delivered by the detector, in turn updating the value for the interface pressure at the location of said detection zone.

The processor system may also be arranged to establishes a map of the interface pressures between the two bodies at a given instant. The processor system may be arranged to update the map, in particular whenever a detector changes state. In a variant, the map may be updated at predetermined time intervals, e.g. regular time intervals, in particular time intervals lying in the range 1 second (s) to 2 days, depending on the application.

The apparatus may be arranged to limit the inflation rate of the detection zones and/or to limit the quantity of inflation fluid in the detection zones, so as to avoid damaging them.

The apparatus may also be arranged to detect a leak from one or more detection zones.

The processor system may be arranged to detect at least one soft point and/or hard point.

The term "soft point" is used to mean a location in the interface where the pressure is lower, e.g. by a factor of 2, or even 5 or 10, or even more, e.g. 30, than the mean pressure exerted between the bodies. At this location, the pressure measured by a detection zone or by a small number of detection zones between the two bodies is lower than the pressures measured by the adjacent detection zones, and in particular lower than a predetermined threshold, which threshold may be a function of the pressure measured by the adjacent detection zones, for example. By way of example, the mean pressure exerted between the bodies may be 0.03 bars, and the pressure at a soft point may be 0.001 bars.

It is also possible to detect a soft point by measuring spacing that is greater between the facing regions at the location of one detection zone than between the facing regions of the envelopes of the adjacent zones.

The term "hard point" is used to mean a location in the interface where the pressure is higher, e.g. by a factor of 2 or 5 or 10, or even more, than the mean pressure exerted between the bodies. At this location, the pressure measured by a detection zone or a small number of detection zones between the two bodies is higher than the pressures measured by the adjacent detection zones, and in particular higher than a predetermined threshold, which threshold may be a function of the pressure measured by the adjacent detection zones, for example. By way of example, the mean pressure may be 0.03 bars and the pressure at a hard point may be 0.4 bars.

It is also possible to detect a hard point by measuring a spacing that is smaller between the facing regions at the location of one detection zone than between the facing regions of the envelopes of the adjacent regions.

A soft or hard point can represent, for example, a surface irregularity or the presence of a predetermined organ in a medical application or an obstetric application, in particular.

In another of its aspects, the invention also provides a method of measuring the interface pressure between two bodies, the method being characterizable by the fact that it comprises the following steps:
    placing a sensor as defined above between the two bodies;
    delivering a fluid into the detection zones of the sensor and causing the pressure within the detection zones to vary; and
    determining the interface pressure between the two bodies at a given instant at the location of a detection zone on the basis of information delivered by the detector of the detection zone.

The method may also include the step consisting in establishing a map of the measured interface pressures. This map may be updated regularly, e.g. at time intervals that may lie in the range 1 s to 2 days.

The method of the invention may be implemented to measure the interface pressure between two surfaces of two soft bodies, or of a soft body and a hard body, or within a soft body, in particular between two surfaces of at least one soft body selected from the following list: a portion of the human body or a body simulating such a portion, in particular the head of a fetus, muscles, skin, mucous membranes, internal cavities; between a portion of the human body and an element interacting with the human body, e.g. a seat, a mattress, garments, the inside of a helmet, elastic stockings or fabric; to determine the hardness of a textile, of a lining material, of an elastomer; to determine the state, in particular the ripening state of produce, in particular vegetables or fruit by determining their hardness.

In another of its aspects, the invention also provides a method of detecting at least one soft point, the method being characterizable by the fact that it comprises the following steps:
    placing a sensor as defined above between the two bodies;
    delivering a fluid into the detection zones of the sensor and causing the pressure inside the detection zones to vary;
    determining the interface pressure between the two bodies at a given instant at the location of a detection zone on the basis of the information delivered by the detector of the detection zone; and
    deducing therefrom the presence and the location of at least one soft point.

In another of its aspects, the invention also provides a method of detecting at least one hard point, the method being characterizable by the fact that it comprises the following steps:
    placing a sensor as defined above between the two bodies;
    delivering a fluid into the detection zones of the sensor and causing the pressure inside the detection zones to vary;
    determining the interface pressure between the two bodies at a given instant at the location of a detection zone on the basis of the information delivered by the detector of the detection zone; and
    deducing therefrom the presence and the location of at least one hard point.

In another of its aspects, the invention also provides an obstetric forceps comprising two blades each having an inside face for coming into contact with the head of a fetus or a body simulating such a head, and an outside face for coming into contact with the pelvic walls or a body simulating such walls, the forceps including at least one sensor as defined above.

A forceps fitted with such a sensor makes it possible to monitor the pressure exerted on the head of the fetus while the forceps is in use, and to change the positioning of the forceps immediately if the sensor detects a soft point such as an eye, a hard point such as a bone, or indeed asymmetry between the pressures exerted by the blades. The forceps may also be used for training doctors or students by being used on a body simulating the head of a fetus.

At least one sensor may be placed on the inside face of at least one of the blades of the forceps. At least one sensor may be placed on the outside face of at least one of the blades of the forceps. The sensor(s) disposed on the blade(s) of the forceps may comprise a plurality of detection zones, e.g. more than ten detection zones, for example 16 or 20 detection zones each, these detection zones being placed in particular around the periphery of one of the faces of at least one blade.

The blades of the forceps may be covered in at least one flexible protective cover that also covers the detection zones of the sensor. The protective cover may be sterile. It may be discarded prior to the forceps being used. In a variant, The protective cover may cover the sensors of the forceps in use, with the cover then serving to protect the sensor(s) while also enabling interface pressure to be measured because of its own flexibility.

In another of its aspects, the invention also provides the use of a sensor as defined above in any one of the following devices: an anti-sore device, mattress, seat, in particular car seat, garments, helmet, elastic stockings or fabric, a device for grasping or clamping a body that is soft and/or of irregular shape and/or of fragile nature, a hydraulic or pneumatic lifting device, or a device for placing in an internal cavity of the human body, or a device for measuring the degree of ripening of produce, in particular fruit or vegetables.

BRIEF DESCRIPTION OF THE DRAWINGS

The invention can be better understood on reading the following detailed description of non-limiting embodiments thereof, and on examining the accompanying drawings, in which:

FIG. 25 is a diagrammatic and fragmentary axial section view showing a car seat provided with sensors of the invention together with the pelvis of a person sitting thereon;

FIG. 26 is a diagrammatic section view showing the sensors that can be fitted to the seat of FIG. 25;

FIG. 27 is a fragmentary view showing one of the sensors of FIG. 26 from above one side;

FIG. 28 is a fragmentary view of the FIG. 26 sensor in plan view seen from the other side relative to that shown in FIG. 27; and FIG. 29 is a diagram showing a grasping or clamping system provided with sensors of the invention.

MORE DETAILED DESCRIPTION

Pressure Measurement Apparatus

Figure 1:
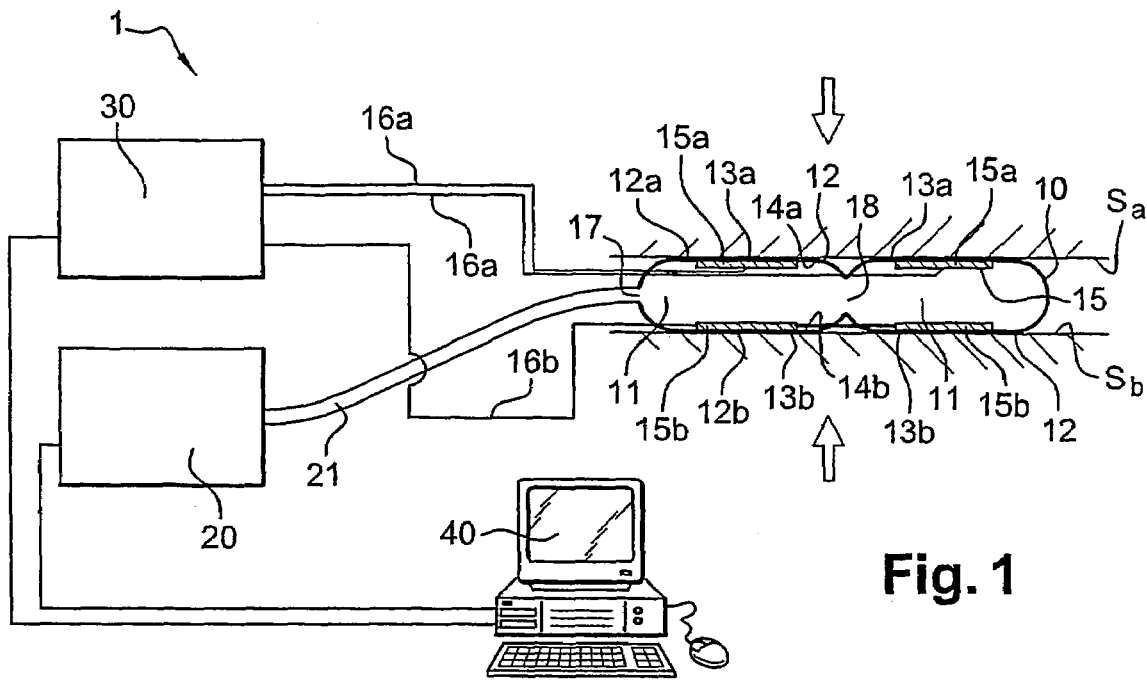
FIG. 1 is a diagrammatic view of an example of interface pressure measurement apparatus made in accordance with the invention.

FIG. 1 show an example of apparatus 1 for measuring the interface pressure between two surfaces Sa and Sb that may be defined by living or inanimate bodies that are soft, deformable, or hard, and of arbitrary shape.

The apparatus 1 comprises at least one sensor 10 enabling interface pressure to be measured, a pressure generator 30 associated with the sensor 10, and a processor system 30 for processing the information delivered by the sensor 10.

In the example shown, the pressure generator 20 and the processor system 30 are connected to a microcomputer 40 serving, for example, to control the pressure generator 20 as a function of information received from the processor system 30.

In a variant that is not shown, the pressure generator 20 and the processor system 30 are made in such a manner as to operate autonomously, independently of any connection with a microcomputer.

In another variant, the processor system 30 and the pressure generator 20 may be arranged to exchange information between each other and/or with a remote computer with or without a portable terminal, using a telephone network or a short distance wireless connection network, e.g. of the Bluetooth☐ or Wi-Fi☐ type.

The pressure generator 20 may comprise, for example, an electromechanical member such as a diaphragm pump or a peristaltic pump. The fluid filling the detection zones is constituted, for example, by a gas such as air, or by a liquid, preferably of low viscosity, and for example electrically insulating.

As can be seen in FIG. 1, the sensor 10 comprises two detection zones 11 each being formed inside an inflatable envelope 12 which is made in the example described out of a fine elastomer membrane. By way of example, the thickness of the membrane lies in the range 0.1 mm to 1 mm, with the membrane being made of polyvinylchloride (PVC) or polyurethane (PU) for example.

The envelopes 12 of the detection zones 11 may be made by bringing together and using heat-sealing or adhesive to bond together two membranes that are were initially independent, or that come from a single membrane that is folded in half and assembled together so as to form the detection zones 11.

It is also possible to make the envelope of a detection zone or of a plurality of detection zones by injection or blow-molding, or by rotary molding.

The detection zones can be made independently, and then brought together so as to make them intercommunicate, or they can be united as from manufacture.

In the example described, each envelope 12 presents two opposite regions 12a and 12b having respective outside faces 13a and 13b that come into contact at least in part with the surfaces Sa and Sb. The opposite regions 12a and 12b also present respective inside faces 14a and 14b on which there are placed at least two elements 15a and 15b constituting a detector 15 suitable for delivering information to the processor system 30 associated with the spacing between the opposite regions 12a and 12b. In the example shown, these elements 15a and 15b comprise electrical conductors capable of coming into contact with each other in order to close an electrical circuit between two respective lines 16a and 16b connected to the processor system 30.

In the example described, the electrical conductors 15b of the two detection zones 11 are electrically connected in series and the electrical line 16b is thus common to all of the detectors 16, e.g. being connected to electrical ground. The processor system 30 receives the two electrical lines 16a that are electrically insulated and connected respectively to the elements 15a of the detection zones 11. The number of lines 16a is preferably equal to the number of detection zones 11 of the sensor 10.

The electrical conductors 15a and 15b can be made by etching a metal on a flexible backing medium, e.g. by etching nickel on polyimide. The conductors may be applied and secured to the opposite regions 12a and 12b of the envelope by adhesive, heat-sealing, mechanical fastening, or in some other way.

The electrical conductors may also be made by being printed directly on the membrane of the envelope, or by dual injection of material while injecting the envelope.

The detect associated with each detection zone need not have electrical conductors designed to come into contact with each other, without that going beyond the ambit of the present invention. In a variant that is not shown, at least one of the detection zones 11 may implement, for example, a detector that is capacitive, being arranged to measure the spacing between the regions 12 or a detector that is inductive, optical, or thermal.

As can be seen in FIG. 1, the sensor 10 also includes an opening 17 made in the envelope of a detection zone 11, so as to enable the inside of the corresponding detection zone to communicate, via a duct 21, with the pressure generator 20. In the example shown, the two detection zones 11 also communicate internally with each other via a passage 18, thus enabling the pressures in the detection zones 11 to be balanced.

The duct 21 may be made integrally with the envelope 12, for example.

Figure 4:
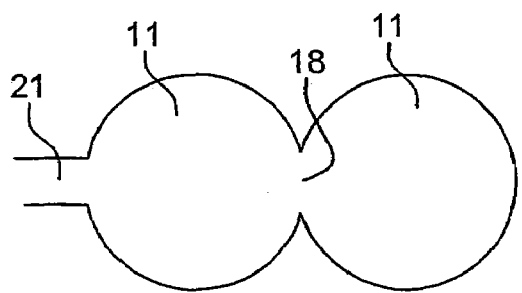
FIGS. 4 to 9 are fragmentary diagrams showing some examples amongst others of ways in which the detection zones can be arranged.

In FIG. 4, it can be seen that when observed in a direction parallel to the direction in which the component elements 15a and 15b of the detects move towards each other, in plan view, each of the detection zones 11 can present an outline that is substantially circular.

Figure 2:
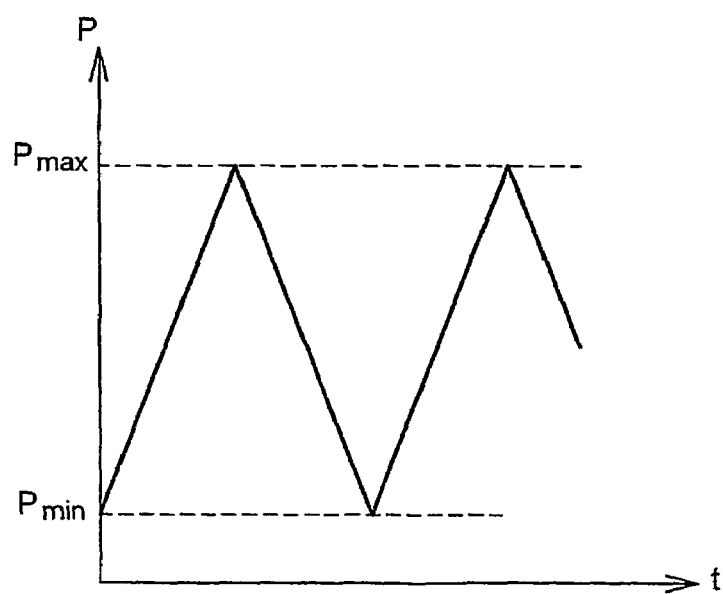
FIGS. 2 and 3 show examples of how pressure varies in the detection zones as a function of time.
Figure 3:
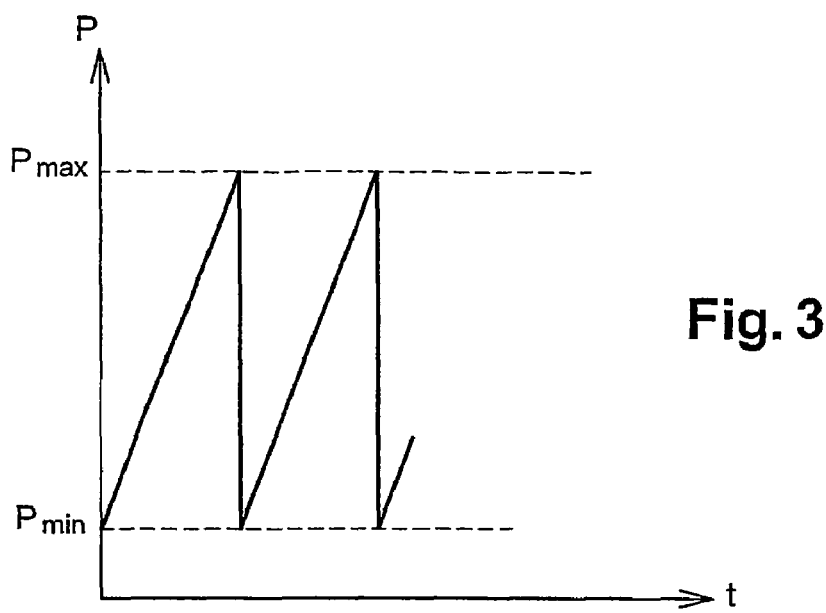

The generator 20 is arranged in such a manner as to act on the pressure of the fluid inside the duct 21. The generator 20 may be arranged to cause the pressure to vary in sawtooth manner, for example, with a triangular profile that is either symmetrical as shown in FIG. 2 or asymmetrical as shown in FIG. 3. The pressure could also be varied in some other way, e.g. sinusoidally, etc. The pressure may vary with a period lying in the range 0.5 s to 1 hour (h), for example. The period of the pressure variation function should be much greater than time constant for balancing pressure in the detection zones, for example.

As a function of the pressure that exists inside the detection zones 11, these zones provide greater or smaller opposition to flattening under the effect of the interface pressure between the surfaces Sa and Sb.

When the pressure inside the detection zones becomes lower than a predetermined value, the electrical conductors 15a and 15b of at least one detection zone 11 can come into electrical contact with one another, and such contact can be detected by the processor system 30. At the moment when contact is made, that means that the pressure that exists in the detection zone has become less than the interface pressure, at least locally. When the contact is broken, that means that the pressure that exists inside the detection zone has become greater than the interface pressure at the location of the corresponding detection zone.

The minimum pressure $P_{min}$ and the maximum pressure $P_{max}$ applied during scanning can be predetermined and can have, for example, respective values lying in the range 0.001 bars to 0.05 bars for living tissue (respectively higher and lower for other applications).

In a variant, the minimum pressure may be determined by the last detection zone of the sensor whose detector changes state after the sectors in all of the other detection zones have already delivered this information while the pressure is decreasing from the maximum pressure.

Similarly, the maximum pressure can be determined by the last detection zone of the sensor to change state corresponding to contact being lost between the opposite regions of the envelope, after the detectors in all the other detection zones have already given this information during an increase in pressure from the minimum pressure.

For each period, the maximum pressure and the minimum pressure can thus vary without being determined by the same detection zones.

The pressure generator 20 is arranged to limit the rate at which the detection zones are inflated and to limit the degree to which the detection zones are inflated, in particular for the purpose of limiting any risk of damaging a detection zone. The inflation volume of a detection zone may be less than or equal to 1 cubic millimeter ($mm^3$) for example.

In order to limit the inflation rate, the apparatus 1 in the example shown includes a flow meter connected to a solenoid valve that interrupts the flow when its rate exceeds a predetermined value much greater than its value in use.

To limit the degree to which the detection zones are inflated, the apparatus 1 in the example shown includes a volume-measuring meter which delivers information to the pressure generator 20 concerning the volume of fluid that has been delivered into the detection zones.

A safety valve (not shown) may be connected, where appropriate, to the duct 21 in order to enable the fluid to escape in the event of pressure rising too high.

The flow meter and the volume meter are integrated in the pressure generator 20 in the example shown and they are not shown in the drawing, however, in a variant, they could be independent or received in other components of the apparatus 1.

The processor system 30 is arranged to sense and process information delivered by the detectors 15 of the detection zones 11 of the sensor 10 and to determine for each detection zone 11 the interface pressure at the location of said detection zone at a given instant.

The change of state of the detector in a detection zone 11 provides information about the value of the interface pressure at the location of said detection zone. This can make it possible for the processor system 30 to draw up a map of the interface pressures in real time.

The processor system 30 may also be arranged to detect points that are soft or hard, for example by comparing the pressure value measured for each detection zone with pressure values measured by the adjacent detection zones.

The apparatus 1 is also advantageously arranged to detect degradation of a detection zone, in particular a leak from a detection zone. For example, prior to placing the sensor 10 between the surfaces Sa and Sb, the pressure generator 20 may inflate the detection zones to a predetermined pressure and detect any variation in pressure. If the pressure decreases, that can mean that at least one of the detection zones is suffering from fluid leakage.

In the example shown in FIG. 1, the passage 18 enabling the detection zones 11 to communicate with one another is situated in a zone in which the envelopes 12 of the detection zones 11 are assembled together, however the detection zones 11 may be arranged in some other way without that going beyond the ambit of the present invention.

For example, the envelope 12 of the detection zones 11 may be made as a single piece, e.g. with lines or spots of heat-sealing defining the detection zones 11, these lines or spots of heat-sealing also contributing, where appropriate, to holding the elements constituting the detectors 15 on the envelopes.

Variant Arrangements for the Detection Zones

FIGS. 5 to 9 show various examples, amongst others, of possible arrangements for the detection zones.

In these figures, the elements constituting the detectors are not shown in order to clarify the drawing.

Figure 5:
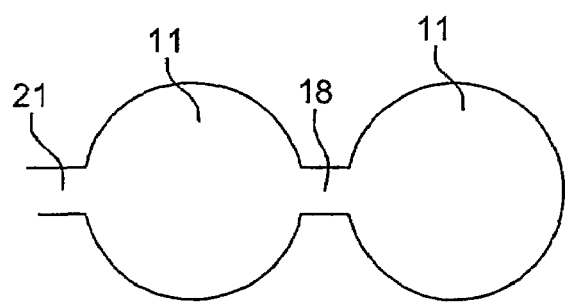

Two detection zones may communicate via a passage 18 constituted by a portion of duct, as can be seen in FIG. 5.

Figure 6:
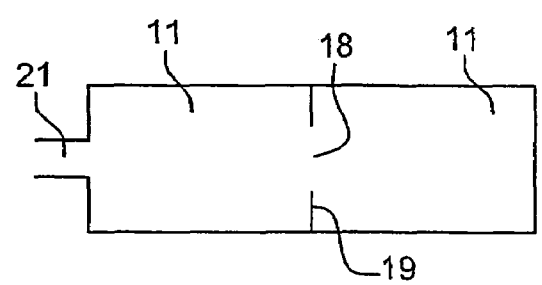
Figure 7:
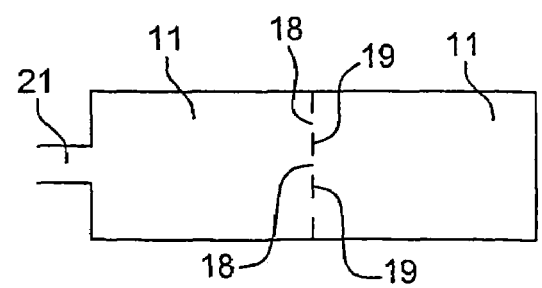

When observed in plan view, the detection zones 11 may be polygonal in shape, e.g. rectangular as shown in FIG. 6. The passage 18 whereby the detection zones communicate can then be defined by lines of sealing 19 uniting opposite regions of the envelopes. The passage 18 may be a single passage or it may be subdivided into a plurality as can be seen in FIG. 7.

Figure 8:
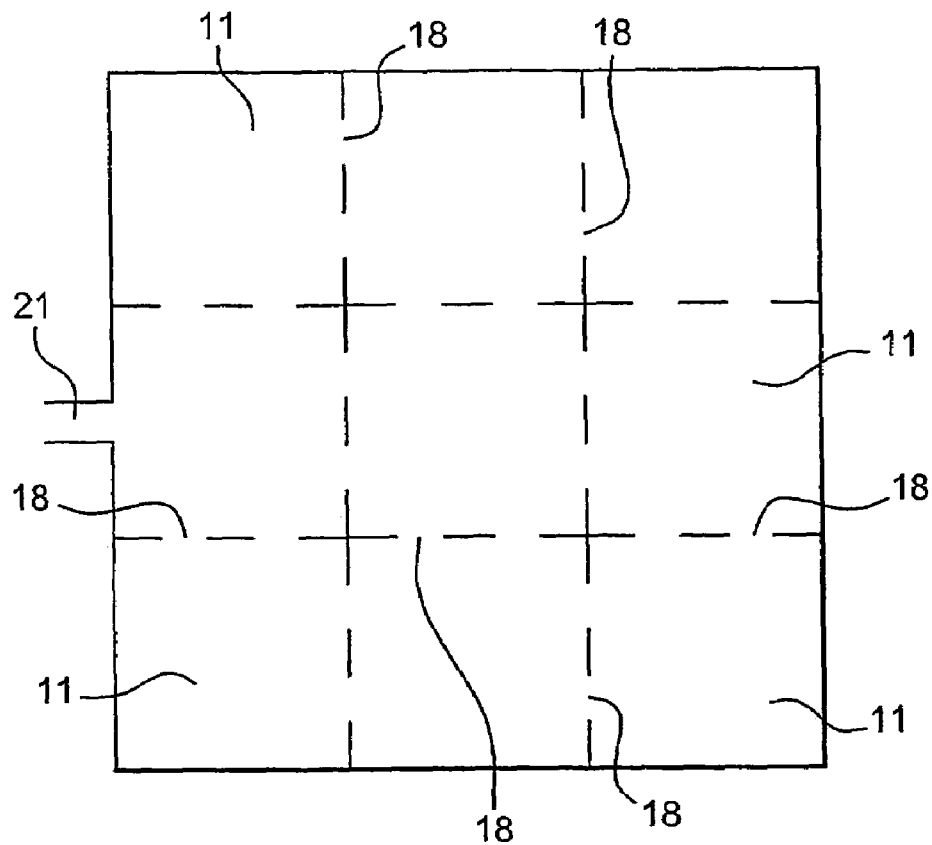

FIG. 8 shows an arrangement of detection zones 11 in a two-dimensional array, the zones communicating between one another in at least two directions, e.g. via passages 18 formed between lines or spots of the sealing.

Figure 9:
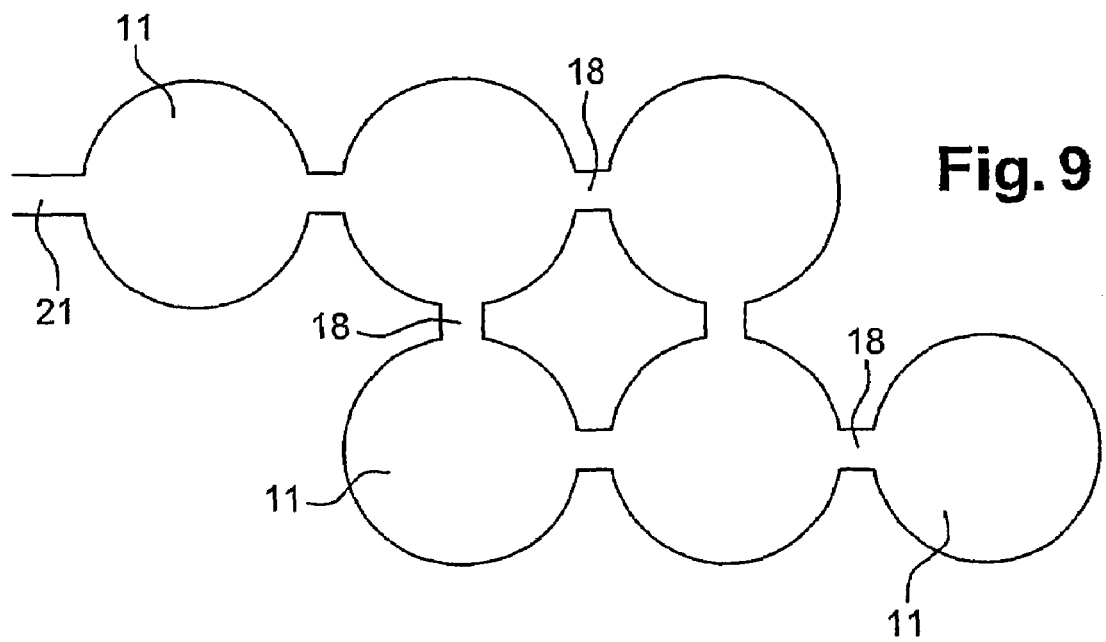

FIG. 9 shows another possible arrangement of detection zones 11, in which they communicate with one another via passages 18 constituted by portions of duct, these ducts possibly being made integrally with the walls of the envelopes of the detection zones, where appropriate.

The detection zones may be arranged between one another in such a manner as to adapt to the shapes of the bodies at which interface pressure is to be measured. In particular, they can be arranged in a three-dimensional array.

Variant Embodiments of the Electrical Conductors

There follows a description with reference to FIGS. 10 to 18 of various possible shapes amongst others for making the electrical conductors.

Figure 10:
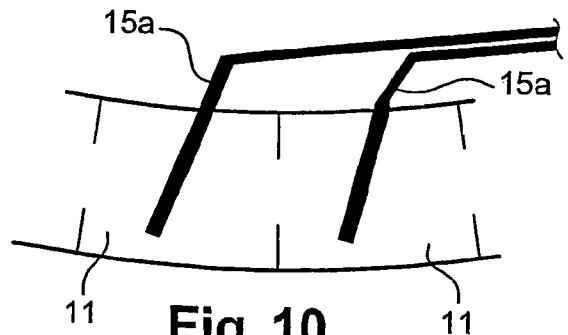
FIG. 10 is a diagrammatic and fragmentary view of an example of an arrangement of an electrical conductor on one of the regions of the detection zone envelope.

The conductors 15*a* secured to one of the regions of the detection zones 11 may be in the form of two rectilinear conductor strips, as shown in FIG. 10. These conductors may extend transversely relative to a longitudinal axis of the sensor.

Figure 11:
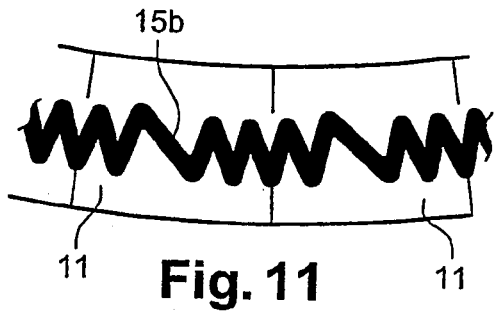
FIG. 11 is a diagrammatic and fragmentary view showing an example of an arrangement for an electrical conductor on another region of the detection zone envelope.

The conductors 15*b* which may be electrically interconnected in series as mentioned above, may be in the form of a conductive strip extending along a non-rectilinear path, and in particular a zigzag-shaped path, as can be seen in FIG. 11, for example.

Figure 12:
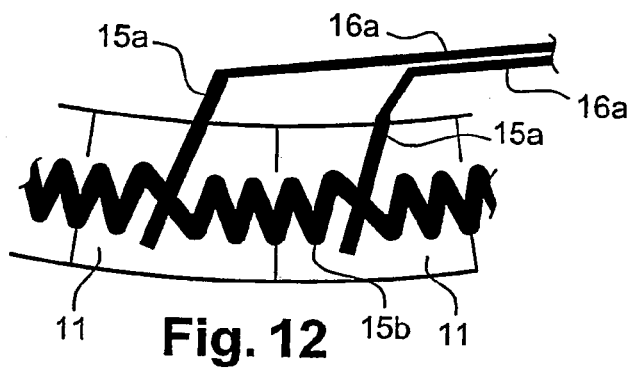
FIG. 12 is a plan view showing an example of the voltage positioning between the electrical conductors of FIGS. 10 and 11.

The conductors 15*a* are placed in such a manner as to intersect the conductors 15*b* when the opposite regions of the detection zones are pressed one against another, as shown in FIG. 12.

Figure 13:
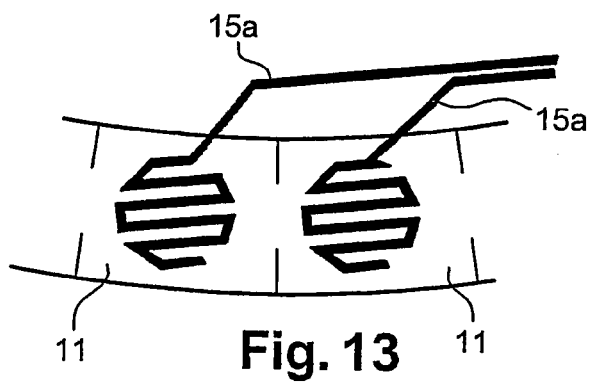
FIGS. 13 to 15 are views respectively analogous to FIGS. 10 to 12 showing another configuration for the electrical conductors.
Figure 14:
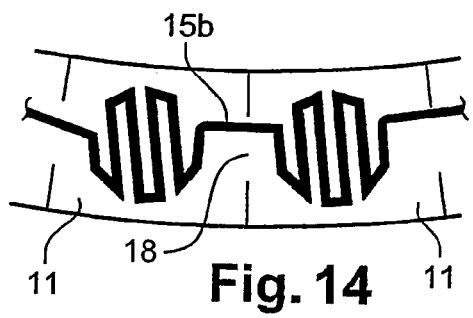
Figure 15:
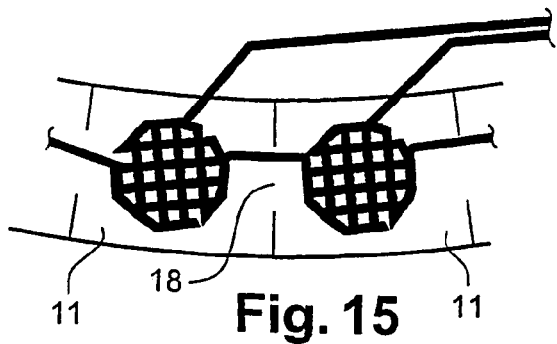
Figure 16:
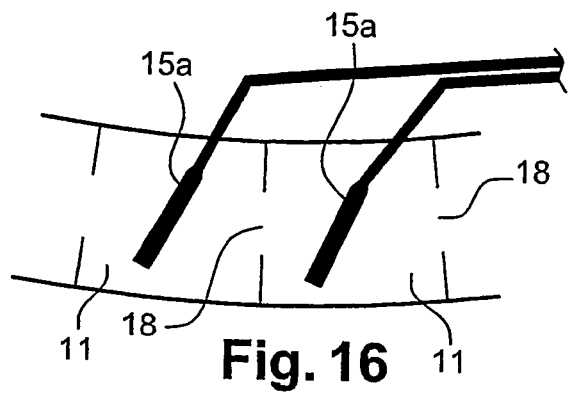
FIGS. 16 to 18 are views respectively analogous to FIGS. 10 to 12, showing yet another element of a configuration of the electrical conductors.
Figure 17:
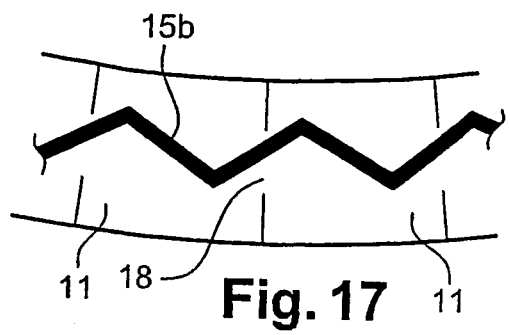
Figure 18:
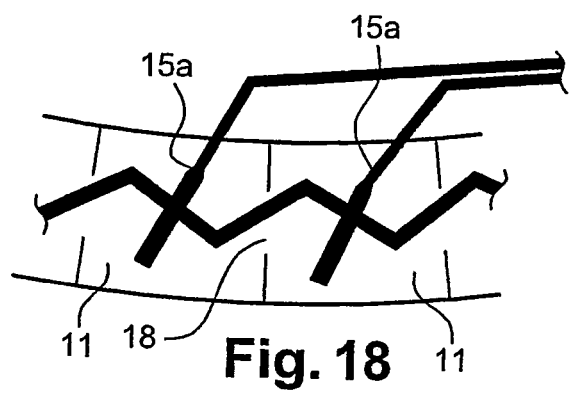

The conductors 15*a* and 15*b* can be given other shapes, for example zigzag-covered spots, as shown in FIGS. 13 and 14, thus making it possible to achieve a large contact area. The conductors 15*a* may also be similar to those of FIG. 11. can the conductor 15*b* may extend in a sawtooth configuration, as shown in FIGS. 16 to 18.

Multiple Fluid Inlets

Figure 19:
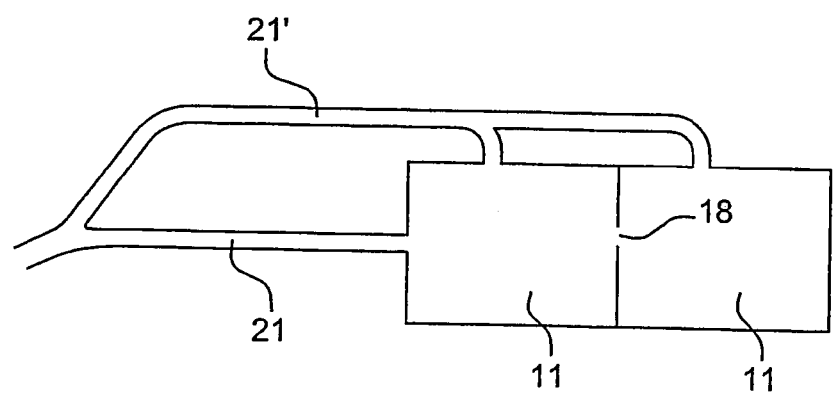
FIG. 19 shows that it is possible to provide more than one fluid inlet per detection zone.

As shown in FIG. 19, at least one detection zone may have more than one fluid inlet. In FIG. 19, there can be seen a second duct 21' connected to the pressure generator 20 for serving each of the detection zones 11. This duct 21' may be connected directly to the pressure generator 20, or in a variant to the duct 12. The duct 21' makes it easier to maintain the detection zones 11 at substantially the same pressure at a given instant, particularly if the passage 18 should be blocked momentarily, e.g. by opposite regions of a few detection zones coming into contact under the effect of pressure being exerted between the surfaces Sa and Sb. Under such circumstances, the detection zone 11 furthest from the pressure generator 20 could be maintained at a determined pressure because of the presence of the duct 21'.

Variant Embodiments of the Envelopes

The envelopes 12 of the detection zones 11 of the sensor 10 may be made in various ways.

Figure 20:
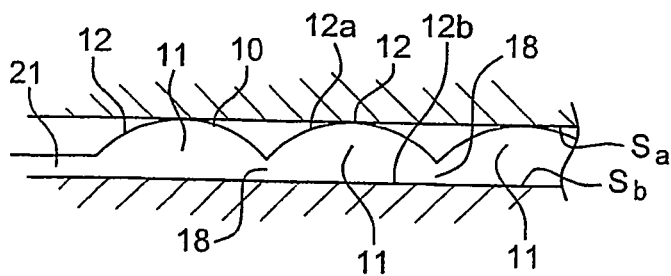
FIG. 20 is a diagrammatic and fragmentary view in axial section showing another example of a sensor of the invention.

An envelope 12 may be flexible completely or in part only. In particular, it may include a portion that coincides with the surface of one of the bodies for which it is desired to measure the interface pressure relative to another body, as shown in FIG. 20. In this example, the surface Sb constitutes, for each detection zone 11, the region 12*b* of the envelope 12, whereas the region 12*a* is constituted by a flexible membrane that comes into contact with the surface Sa. By way of example, this membrane is bonded by heat-sealing or adhesive to spots of the surface Sb in such a manner as to form the detection zones 11 and the passages 18 between the detection zones. Under such circumstances, the sensor 10 is secured to the body defining the surface Sb. The duct 21 is also made using the surface Sb in the example shown.

The detectors in the detection zones are not shown in this figure in order to clarify the drawing.

Figure 21:
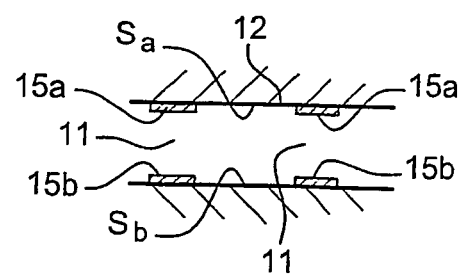
FIG. 21 is a diagrammatic and fragmentary view in axial section showing another example of a sensor of the invention.

The terms "envelope" and "detection zones" should not be interpreted in limiting manner. Thus, the envelope may be common to a plurality of detection zones even though each of them retains its own detector. As shown in FIG. 21, it is not essential for two adjacent detection zones 11 to have a partition between them. Two adjacent detection zones 11 may alternatively have a partition so as to form cells.

A sensor made in accordance with the invention can be used in numerous applications, and in particular in the fields of medicine or obstetrics.

An Example of Application to a Forceps

Figure 22:
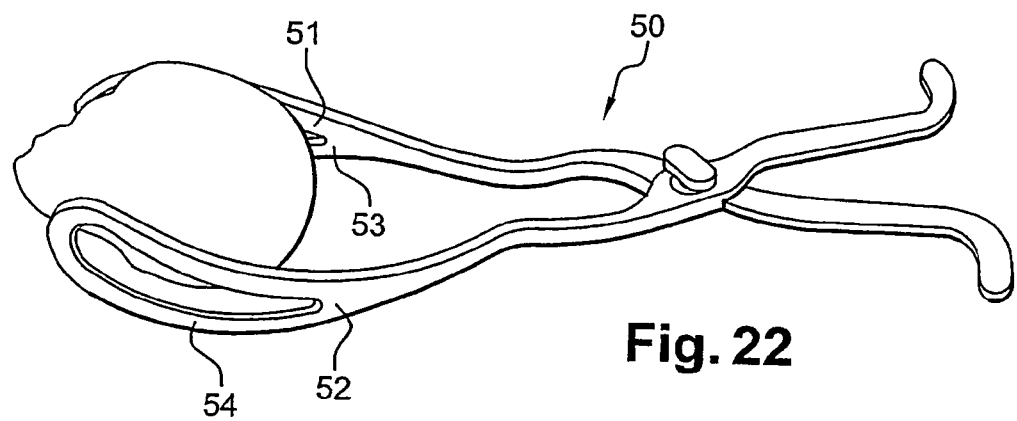
FIG. 22 is a diagrammatic and perspective view showing a pair of forceps fitted with sensors in accordance with the invention.

By way of example, FIG. 22 shows a forceps 50 comprising two blades 51 and 52, each presenting an inside face 53 and an outside face 54.

Figure 23:
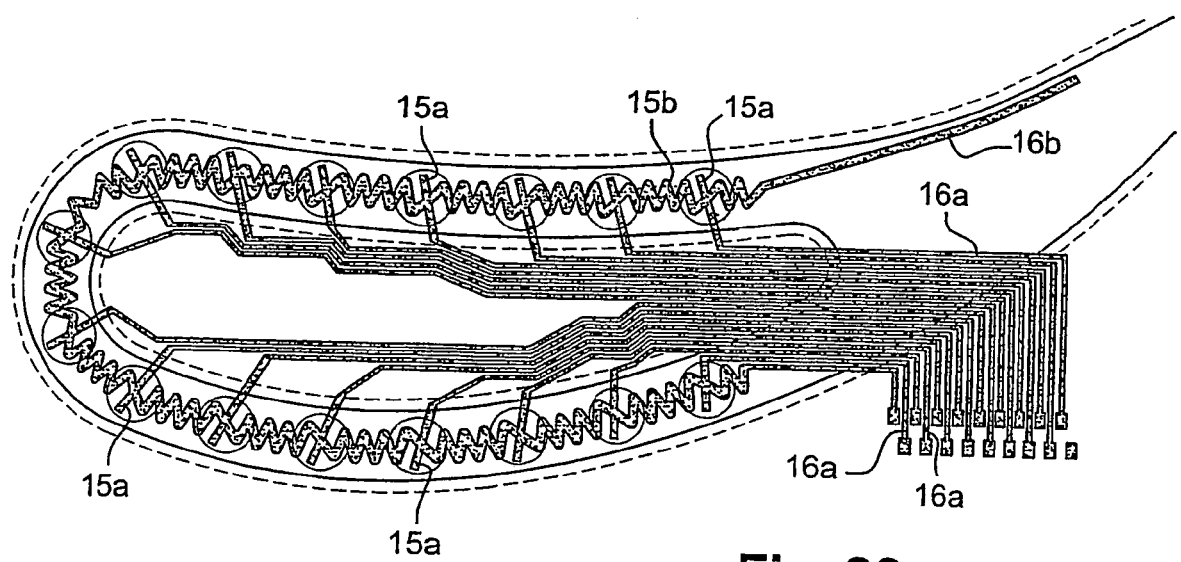
FIG. 23 is a diagrammatic view of one example of a sensor suitable for fitting to the forceps of FIG. 22.

In the example shown, the forceps 50 carry two sensors 10 (not shown in FIG. 22 in order to clarify the drawing) disposed respectively on each of the inside faces 53 of the blades 51 and 52. Each sensor 10 comprises a plurality of detection zones disposed around the periphery of its corresponding face, as can be seen in FIG. 23. By way of example, the number of detection zones 11 lies in the range 10 to 20, e.g. being 16 as shown in the drawing.

An advantage of having at least one sensor made in accordance with the invention on a forceps is to measure the pressures exerted on the head of the fetus by the blades of the forceps, to detect a soft point as might be constituted by an eye, or a hard point that might be constituted by a bone.

When the sensors are present on the inside faces 53 of the two blades 51 and 52, it is also advantageous to verify that the pressures-exerted on the head of the fetus are symmetrical so as to avoid excessive pressure on one side of the head.

A flexible protective cover represented by discontinuous lines in FIG. 23 may cover the blades and the sensor(s) before and during utilization. The cover is preferably sterilizable together with the sensor, and in particular is suitable for being raised to a temperature greater than or equal to 130° C.

The microcomputer 40 in the example of FIG. 1, when used with interface pressure sensors on a forceps 50, may be arranged to enable the person handling the forceps to see a map of the pressures being exerted.

Figure 24:
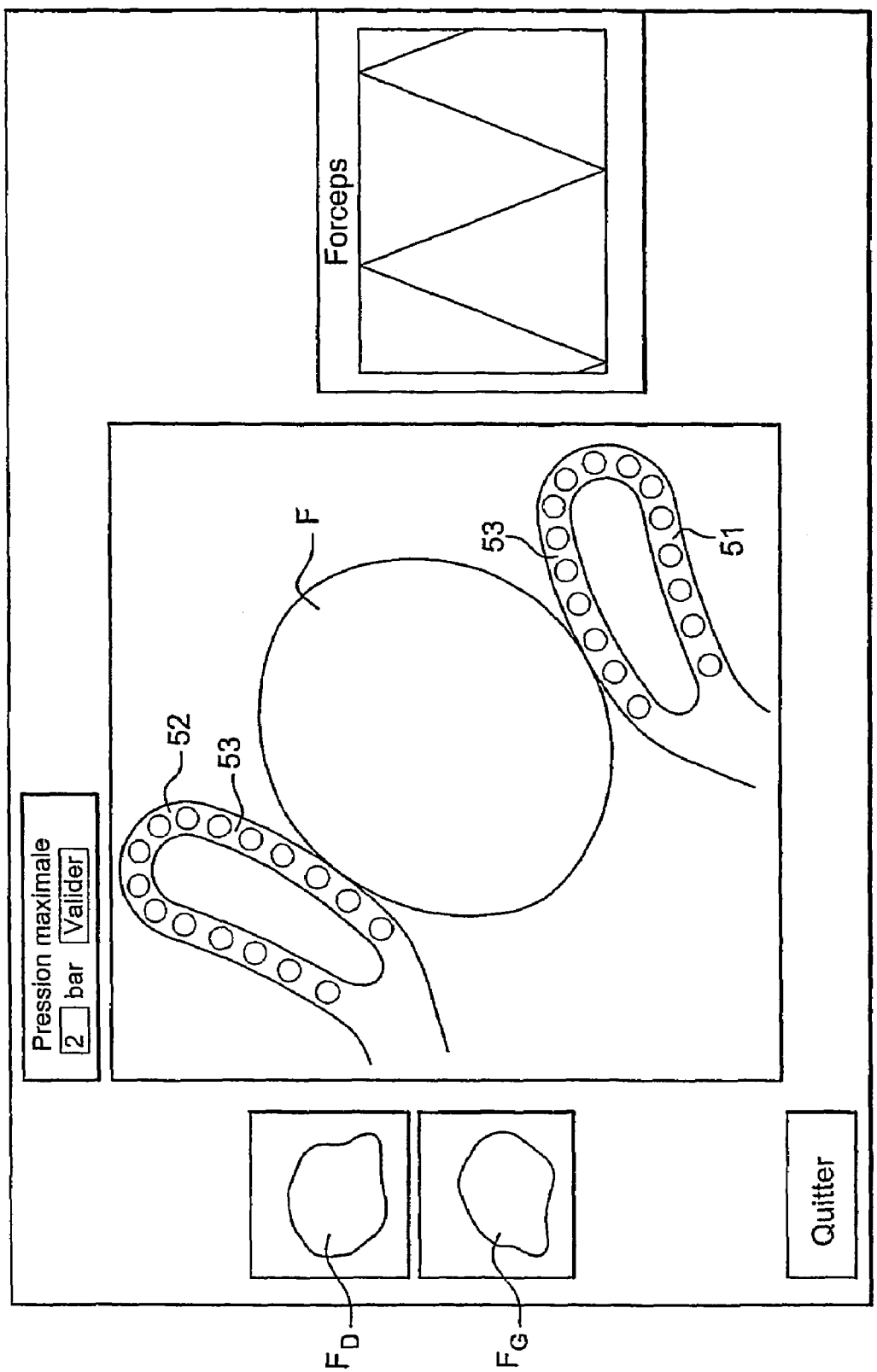
FIG. 24 shows an example of how information associated with the use of a sensor of the invention can be presented.

FIG. 24 shows an example of a screen that can be observed by the obstetrician by using the forceps 50.

In this figure, there can be seen a diagram of the head of a fetus F, the blades 51 and 52 of the forceps having the sensors 10 disposed on their inside faces 53. These sensors are shown in a different color (not visible in the figure) depending on whether the corresponding electrical conductors are or are not making contact. In a variant not shown, this indication is provided by means other than a color, for example by a numeral or a histogram, etc.

The pressure in the detection zones varies in sawtooth manner, e.g. with an amplitude of 0.2 bars. The right and left profile views $F_R$ and $F_L$ of the head of the fetus can serve to illustrate the pressures to which each portion of the head of the fetus F is being subjected.

Application to Preventing Sores in the Sitting Position

Another application is shown by way of illustration in FIG. 25 to 28.

This example relates to measuring the interface pressure between the seat proper of a seat S and the buttocks, in particular the ischia I of a patient whose pelvis is shown diagrammatically in FIG. 25. The seat includes at least one sensor as described above, and in particular two sensors in the example shown.

The two interface pressure sensors 10 are disposed on the seat proper S under the ischia I at the location where the interface pressure is particularly high, possibly being as much as 300 millimeters of mercury (mmHg).

As can be seen in FIG. 26, the admission of fluid, in particular air, in the direction of the arrow is common to both sensors 10 in the example shown, but it would not go beyond the ambit of the invention for each sensor to have its own specific fluid admission.

Each sensor has a plurality of detection zones 11, e.g. 32 such zones disposed at the intersections of a grid in the example shown, thereby making data processing easier. The detection zones 11 are grouped together in groups of two or three within a portion of the sensor envelope that is substantially in the elongate shape of a glove finger. The portions of elongate glove finger shape in the envelope thus occupy two facing rows.

The distance between pairs of sensors 10 may be 2 cm, the diameter of a sensor may be about 14 cm, and the cross-section of a glove finger-forming portion may be about 1 cm². The elongate shape of the glove finger portions of the envelope 12 enable the membrane of the sensor to withstand an internal pressure that is high without risk of breaking. The presence of 12 portions of elongate shape improves the total strength of the sensor membrane.

The envelope 12 of the detection zones comprises two opposite regions 12a and 12b shown respectively in FIGS. 27 and 28.

In the region 12a as shown in FIG. 27, each detection zone 11 carries an element 15a of a detector 15 constituted in the example shown by an electrical conductor. Each element 15 of a detection zone 11 is connected via an independent electrical line 16a to the processor system 30 (not shown in the figure). The lines 16a are electrically insulated. In FIG. 27, only some of the lines 16a are shown for reasons of clarity, but all of the elements 15a are connected by lines 16a to the processor system. The eight lines 16a shown constitute a bus.

In FIG. 28, there is shown a portion of the opposite region 12b. Each detection zone 11 includes an element 15b of a detector 15. The elements 15b are likewise electrical conductors in the example shown, and they are all electrically interconnected, with the electrical line 16b thus being common to all of the detectors 15 and being connected to electrical ground, for example.

The lines 16a and 16b present undulations in the example shown, thus giving these lines elasticity in all dimensions, thereby reducing the risk of the elements 15a and 15b or the lines 16a and 16b breaking.

In operation, the pressure generator 20 causes pressure to sweep between a minimum pressure and a maximum pressure.

The state of the contacts between the regions is displayed on a computer screen (not shown), e.g. in real time.

By using sensors disposed on the seat proper of a seat, it is possible to avoid sores forming, where sores constitute a pathology that results from applying too much pressure to living tissue, in particular pressure greater than the capillary perfusion pressure (32 mmHg) over a long period of time.

When prolonged high pressures are detected that can trigger a warning to persons interested, and in particular to care staff who will then take the necessary actions by changing the pressure points or by changing the selected anti-sore support.

Such a device may be for use by people of reduced mobility, of old age, people with chronic and accidental handicaps, such as quadriplegics and paraplegics, people with third-degree burns, or patients during lengthy hospitalization.

It would not go beyond the ambit of the present invention if the seat were to be replaced by a mattress on which the patient is prone.

An Example of an Application to a Member for Grasping or Clamping

Another example of a use for a sensor of the invention is shown in FIG. 29.

This is a device R for clamping or grasping comprising or at least forming a clamp in the form of an artificial hand provided with at least one and in particular a plurality of sensors 10.

Such a device can be of use in robotics, in the development of haptic interfaces, e.g. for the purpose of assisting in performing medical acts during surgical operations.

Examples of Other Applications

The use of a sensor made in accordance with the invention may have a variety of purposes.

For example a sensor may be used with a living being, in particular in the human body, in order to measure pressure in living tissue as an interface between two soft surfaces or between a soft surface and a hard body, or indeed the pressure within a substance that is soft or deformable, e.g. in the internal cavities, and in particular the intestine, the vagina, or the esophagus.

A sensor may also be used for measuring pressures applied to the human body by garments, seats, or helmets for the purposes of studying comfort, by elastic stockings or other garments, e.g. for preventing phlebitis.

A sensor may also be used for taking measurements relating to foods, e.g. for the purpose of testing ripening, e.g. of a fruit as a function of its hardness.

A sensor may also be used for characterizing the pressures and pressure distributions in devices for grasping or clamping.

A sensor may be used for monitoring the interface pressure in mattresses or seats, or for testing the effectiveness of an anti-sore device, e.g. a mattress. It is also possible to measure the propagation of pressure as can be important for massaging and draining blood and lymphatic microcirculation. It may also be used to prevent scars.

A sensor can be used to verify that a hydraulic and pneumatic lifting device is acting uniformly.

In another of its aspects, the invention also provides a mattress including a sensor made in accordance with the invention.

In another of its aspects, the invention also provides a seat, e.g. a vehicle seat or a wheel chair, including at least one sensor as defined above.

In another of its aspects, the invention also provides an anti-sore device including a sensor made in accordance with the invention.

An "anti-sore" device is a mattress, a seat, or a garment, for example, filled with a fluid, e.g. water or a gel, or presenting an ergonomic shape.

In another of its aspects, the invention also provides a garment, in particular an intelligent garment, or a helmet, and including a sensor made in accordance with the invention.

The term "intelligent garment" is used to mean a garment provided with at least one sensor, e.g. a temperature sensor, and/or a cardiac frequency sensor, and/or a breathing frequency sensor, and/or a position sensor, amongst other possibilities. An intelligent garment can be useful for tracking variations in one or more biological and/or physical parameters relating to the person wearing it.

In another of its aspects, the invention also relates to elastic stockings or fabric including a sensor made in accordance with the invention.

In another of its aspects, the invention also provides a device for grasping or clamping soft bodies and/or bodies of irregular shapes and/or of a fragile nature, the device including a sensor made in accordance with the invention.

In another of its aspects, the invention also provides a hydraulic or pneumatic lifting device including a sensor made in accordance with the invention.

Throughout the description, including in the claims, the term "comprising a" should be understood as being synonymous with "comprising at least one" unless specified to the contrary.

What is claimed is:

1. A sensor for sensing an interface pressure between two bodies, the sensor comprising:
    at least two intercommunicating detection zones, each detection zone being formed inside an inflatable envelope for interposing between said bodies and having two opposite regions spaced apart from one another by an amount that depends on an interface pressure between said bodies, each detection zone comprising a detector arranged to deliver information associated with the spacing between the opposite regions, wherein the detector comprises a portion of an element that is common to a plurality of the detection zones, and an element specific to the respective detection zone; and
    a pressure generator configured to deliver a fluid into the detection zones at a pressure that varies in time.

2. A sensor according to claim 1, wherein the at least two detection zones comprises more than two detection zones.

3. A sensor according to claim 1, wherein the number of detection zones ranges from 2 to 100.

4. A sensor according to claim 1, wherein at least one envelope of a detection zone is made at least in part out of a material that is elastically deformable.

5. A sensor according to claim 1, wherein the detection zones are arranged in a two-dimensional array.

6. A sensor according to claim 1, wherein at least one of the detection zones comprises a detector arranged to measure the spacing between the two opposite regions of the envelope of the at least one detection zone.

7. A sensor according to claim 1, wherein the detector is selected from an electrical detector; an optical detector; a magnetic detector; and a thermal detector.

8. A sensor according to claim 7, wherein the detector comprises an electrical detector relying on contact or capacitance.

9. A sensor according to claim 7, wherein the detector comprises an optical detector comprising at least one of an optical fiber detector, a diffraction detector, and an optical focus detector.

10. A sensor according to claim 7, wherein the detector comprises a magnetic detector comprising at least one of an induction detector using a linear wire or a coil, and a Hall effect detector.

11. A sensor according to claim 1, wherein the element that is common to a plurality of the detection zones comprises a portion of an electrical conductor that is common to a plurality of the detection zones.

12. A sensor according to claim 11, wherein the electrical conductor is connected to electrical ground.

13. A sensor according to claim 1, wherein the element specific to the respective detection zone comprises an electrical conductor specific to the respective detection zone.

14. A sensor according to claim 1, wherein the information associated with the spacing between the regions of the envelope comprises binary information.

15. A sensor according to claim 1, wherein the detector comprises at least two elements disposed respectively on each of the inside faces of facing regions of the envelope.

16. A sensor according to claim 15, wherein the at least two elements comprise electrical conductors made by etching on a medium coated in a conductor metal.

17. A sensor according to claim 16, wherein the medium comprises polyimide and the conductor metal comprises nickel.

18. A sensor according to claim 1, wherein at least one detection zone comprises a non-rectilinear electrical conductor.

19. A sensor according to claim 18, wherein the electrical conductor extends in a zigzag configuration.

20. A sensor according to claim 1, further comprising a fluid admission common to all of the detection zones of the sensor.

21. A sensor according to claim 1, further comprising at least one fluid admission external to the detection zones and serving each of them externally.

22. An apparatus according to claim 1, wherein the pressure generator is configured so as to cause the pressure to vary as a continuous periodic function.

23. An apparatus according to claim 22, wherein the periodic function is one of a sinusoidal function and a sawtooth function.

24. An apparatus according to claim 1, wherein the apparatus is configured to detect the last separation between facing regions of a detection zone among a set of detection zones, and to cause the pressure applied by the pressure generator to diminish.

25. An apparatus according to claim 1, further comprising a processor system for processing information delivered by the detector of at least one detection zone.

26. An apparatus according to claim 25, wherein the processor system is configured to respond to information delivered by the detector in a detection zone to determine the interface pressure between the two bodies at a given time at the location of said detection zone.

27. An apparatus according to claim 25, wherein the processor system is configured to establish a map of interface pressures between the two bodies at a given time.

28. An apparatus according to claim 27, wherein the processor system is configured to update said map when a detector changes state or at predefined time intervals.

29. An apparatus according to claim 1, the apparatus being configured to limit the inflation flow rate of the detection zones.

30. An apparatus according to claim 1, the apparatus being arranged to limit the quantity of inflation fluid in the detection zones.

31. An apparatus according to claim 1, the apparatus being configured to detect a leak from one or more detection zones.

32. An apparatus according to claim 1, wherein the processor system is configured to detect a soft point.

* * * * *